(12) United States Patent
Brown

(10) Patent No.: US 7,752,056 B2
(45) Date of Patent: *Jul. 6, 2010

(54) NETWORK MEDIA ACCESS CONTROL SYSTEM FOR ENCOURAGING PATIENT COMPLIANCE WITH A TREATMENT PLAN

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 11/645,439

(22) Filed: Dec. 26, 2006

(65) Prior Publication Data

US 2007/0124179 A1    May 31, 2007

Related U.S. Application Data

(63) Continuation of application No. 10/233,296, filed on Aug. 30, 2002, which is a continuation-in-part of application No. 09/304,447, filed on May 3, 1999, now abandoned, which is a continuation of application No. 08/771,951, filed on Dec. 23, 1996, now Pat. No. 5,933,136.

(51) Int. Cl.
*G06Q 10/00* (2006.01)
*G06Q 50/00* (2006.01)

(52) U.S. Cl. ........................................ 705/2
(58) Field of Classification Search ........... None
See application file for complete search history.

(56) References Cited

U.S. PATENT DOCUMENTS 4,803,625 A * 2/1989 Fu et al. ............... 600/483

5,034,807 A   7/1991 Von (Continued)

FOREIGN PATENT DOCUMENTS

EP    370599    5/1990

(Continued)

OTHER PUBLICATIONS

Alere Medical Inc's First Supplemental Response to Plaintiff's Amended Interrogatory No. 2. Jun. 20, 2008.

(Continued)

*Primary Examiner*—Gerald J. O'Connor
*Assistant Examiner*—Sheetal R Rangrej
(74) *Attorney, Agent, or Firm*—Suiter Swantz pc llo

(57) ABSTRACT

A system and method for controlling patient access to an entertainment program to encourage a patient to comply with a treatment plan. The method includes the step of collecting compliance data from the patient. In one embodiment, the compliance data includes measurements of a physiological condition of the patient as well as patient answers to compliance questions. The method further includes the step of comparing the compliance data to evaluation criteria selected by a healthcare provider to determine if the patient is in compliance with the treatment plan. If the patient is in compliance, access is granted to the entertainment program. If the patient is not in compliance, access to the entertainment program is restricted. In the preferred embodiment, the method includes the additional steps of transmitting and displaying the patient's compliance data and compliance status to the healthcare provider.

9 Claims, 14 Drawing Sheets

U.S. PATENT DOCUMENTS

| | | | |
|---|---|---|---|
| 5,128,752 A | 7/1992 | Von | |
| 5,142,358 A | 8/1992 | Jason | |
| 5,227,874 A | 7/1993 | Von | |
| 5,249,044 A | 9/1993 | Von | |
| 5,329,459 A | 7/1994 | Kaufman et al. | |
| 5,329,608 A | 7/1994 | Bocchieri et al. | |
| 5,339,821 A | 8/1994 | Fujimoto | |
| 5,390,238 A | 2/1995 | Kirk et al. | |
| 5,441,047 A * | 8/1995 | David et al. | 600/483 |
| 5,467,269 A | 11/1995 | Flaten | |
| 5,471,039 A | 11/1995 | Irwin et al. | |
| 5,483,276 A | 1/1996 | Brooks et al. | |
| 5,488,423 A | 1/1996 | Walkingshaw et al. | |
| 5,502,636 A | 3/1996 | Clarke | |
| 5,504,519 A | 4/1996 | Remillard | |
| 5,619,991 A * | 4/1997 | Sloane | 600/300 |
| 5,687,322 A | 11/1997 | Deaton et al. | |
| 5,722,418 A | 3/1998 | Bro | |
| 5,727,153 A | 3/1998 | Powell | |
| 5,743,746 A * | 4/1998 | Ho et al. | 434/332 |
| 5,810,747 A * | 9/1998 | Brudny et al. | 600/595 |
| 5,903,211 A * | 5/1999 | Flego et al. | 340/286.07 |
| 6,151,586 A | 11/2000 | Brown | |

FOREIGN PATENT DOCUMENTS

| | | |
|---|---|---|
| EP | 0251520 | 1/1998 |
| WO | WO-95/09386 | 4/1995 |
| WO | WO-95/20199 | 7/1995 |
| WO | WO-97/08605 | 3/1997 |
| WO | WO-97/12544 | 4/1997 |

OTHER PUBLICATIONS

U.S. Appl. No. 90/010,053—Order Granting Request For Ex Parte Reexamination, Jan. 18, 2008.

90009240_Request_for_Re-examination_6151586_Aug. 1, 2008.

Sep. 1, 1995 Lunt_The_Smart_Cards_Are_Here.

* cited by examiner

TREATMENT PLAN SPECIFICATION SCREEN

PATIENT: JONES, SALLY ▽    DISEASE: DIABETES ▽

SELECT MONITORING TYPE(S)
- [x] GLUCOSE MONITOR
- [x] TELEPHONE QUESTIONS/TEST
- [ ] ON-SCREEN QUESTIONS/TEST
- [ ] INTERACTIVE PROGRAM

SELECT EVALUATION CRITERIA
- [x] MINIMUM GLUCOSE VALUE — 70 MG/DL
- [x] MAXIMUM GLUCOSE VALUE — 120 MG/DL
- [x] NUMBER OF MEASUREMENTS — 14
- [x] MINIMUM TELEPHONE SCORE — COMPLETED
- [ ] MINIMUM ON-SCREEN SCORE — 7
- [ ] MINIMUM PROGRAM SCORE — COMPLETED

MONITORING INTERVAL: 7 DAYS ▽

[OK] [CANCEL]

*FIG. 2*

COMPLIANCE QUESTIONS SCRIPT

"THE FOLLOWING QUESTIONS ARE ON A SCALE OF 1 TO 5, WITH 1 BEING THE WORST OR LOWEST, 3 BEING AVERAGE OR MIDDLE, AND 5 BEING BEST OR GREATEST."

1. "ON A SCALE OF 1 TO 5, HOW WELL ARE YOU MANAGING YOUR DIABETES?"

2. "ON A SCALE OF 1 TO 5, HOW GOOD IS THE CARE YOU RECEIVE FROM THE DOCTOR WHO MANAGES YOUR DIABETES?"

3. "ON A SCALE OF 1 TO 5, HOW HARD IS IT FOR YOU TO FOLLOW YOUR TREATMENT PLAN?"

4. "ON A SCALE OF 1 TO 5, HOW WELL DOES YOUR DOCTOR UNDERSTAND AND RESPOND TO YOUR NEEDS?"

5. "ON A SCALE OF 1 TO 5, HOW HARD IS IT FOR YOU TO CONTROL YOUR BLOOD GLUCOSE LEVEL?"

"PLEASE ANSWER THE FOLLOWING QUESTIONS WITH A NUMERIC ANSWER."

6. "HOW MANY TIMES IN THE PAST 7 DAYS DID YOU HAVE BLOOD SUGAR THAT YOU FELT WAS TOO LOW?"

7. "HOW MANY TIMES IN THE PAST 7 DAYS DID YOU HAVE BLOOD SUGAR THAT YOU FELT WAS TOO HIGH?"

8. "HOW MANY TIMES IN THE PAST 7 DAYS DID YOU CONSULT YOUR DOCTOR ABOUT SOMETHING RELATED TO DIABETES?"

9. "HOW MANY TIMES PER DAY ON AVERAGE DID YOU TEST YOUR BLOOD SUGAR IN THE PAST 7 DAYS?"

10. "HOW MANY SICK DAYS DID YOU HAVE IN THE PAST 7 DAYS?"

*FIG. 5*

NETWORK MEDIA ACCESS CONTROL SYSTEM FOR ENCOURAGING PATIENT COMPLIANCE WITH A TREATMENT PLAN

CROSS REFERENCE TO RELATED APPLICATIONS

The present application is a continuation of U.S. patent application Ser. No. 10/233,296 filed Aug. 30, 2002 which is a continuation-in-part application of U.S. patent application Ser. No. 09/304,447 filed May 3, 1999 (abandoned) which is a continuation of U.S. patent application Ser. No. 08/771,951 filed Dec. 23, 1996, now U.S. Pat. No. 5,933,136. Said U.S. patent application Ser. Nos. 10/233,296, 09/304,447 and 08/877,951 are hereby incorporated by reference in their entirety.

FIELD OF THE INVENTION

The present invention relates generally to access control systems, and in particular to a system and method for controlling a patient's access to an entertainment program to encourage the patient to comply with a treatment plan for a health condition.

BACKGROUND OF THE INVENTION

In recent years, an increasing number of healthcare providers have initiated outpatient or home healthcare programs for their patients. The potential benefits of these home healthcare programs are particularly great for chronically ill patients, such as those suffering from diabetes or asthma, who must treat their diseases on a daily basis. However, the success of these home healthcare programs is currently limited by each patient's initiative and motivation to comply with a prescribed treatment plan for his or her disease.

The most common reason a patient fails to comply with a treatment plan is a lack of motivation to treat the disease when the disease is not causing an immediately recognizable affect. The primary affect of most diseases is pain, and once the pain stops, many patients ignore the disease until the pain returns. Of course, most healthcare issues can be addressed much more effectively through prevention. The challenge is in communicating the preventative concept to a patient in such a way that he or she will be motivated and encouraged to comply with a prescribed treatment plan.

A patient's lack of motivation to comply with a treatment plan also limits the ability of a healthcare provider to aid the patient in treating his or her disease. Many treatment plans require daily monitoring of a physiological condition of the patient, such as blood glucose levels in diabetes and peak flow rates in asthma. Since the patients themselves monitor these conditions in outpatient programs, the provider is often limited to learning each patient's status strictly through patient initiated events, such as an emergency visit or the delivery of the patient's latest medical data. Even with the current availability of remote monitoring devices that store and transmit medical data from a patient's home to a medical clinic, the provider must still wait for medical information whose arrival depends on the patient's initiative.

As a result, the majority of the provider's time is spent with the patients who are the most motivated and eager for treatment, while the greatest medical needs remain with the unmotivated patients who do not visit the provider or transmit their medical data. These unmotivated patients often develop urgent medical needs that could have been prevented with proper plan compliance. Consequently, the cost of treating their diseases is much higher than one might expect given the sophistication of current medical monitoring devices.

The prior art has not taught a restrictive access control system for encouraging a patient's compliance with a treatment plan. However, access control systems have been developed for controlling access to television programming based on the paying of a program fee or the desired censorship of programs containing subject matter deemed unsuitable for all viewers. For example, U.S. Pat. No. 4,768,229 issued to Benjamin et al. on Aug. 30, 1988 describes a restrictive access control system that includes a three-state switch for limiting television tuning access to only designated channels. U.S. Pat. No. 5,550,575 issued to West et al. on Aug. 27, 1996 discloses a viewer discretion television program control system which relies upon suitability ratings and personal identification numbers of household viewers to restrict television program access.

The systems described by Benjamin and West are not directed at motivating a patient to comply with a treatment plan, nor do they have any mechanism for monitoring a patient's compliance or for controlling program access in dependence upon the patient's compliance. Thus, none of the prior art systems for controlling access to an entertainment program encourage a patient to comply with a treatment plan, nor do they provide for remote monitoring of a patient's compliance.

OBJECTS AND ADVANTAGES OF THE INVENTION

In view of the above, it is an object of the present invention to provide a system and method for controlling a patient's access to an entertainment program to encourage the patient to comply with a prescribed treatment plan. It is another object of the invention to provide an access control system that encourages an unmotivated patient to monitor his or her condition and to transmit monitored data to a healthcare provider.

These and other objects and advantages will become more apparent after consideration of the ensuing description and the accompanying drawings.

SUMMARY OF THE INVENTION

The invention presents a system and method for controlling patient access to an entertainment program to encourage a patient to comply with a treatment plan. The method includes the step of collecting in an access control system patient compliance data for determining if the patient is in compliance with the treatment plan. In the preferred embodiment, the compliance data includes measurements of a physiological condition of the patient as well as patient answers to compliance questions.

The method further includes the step of storing in the access control system compliance evaluation criteria selected by a healthcare provider. The compliance data is compared to the evaluation criteria to determine if the patient is in compliance with the treatment plan. If the patient is in compliance, access is granted to the entertainment program. If the patient is not in compliance, access to the entertainment program is restricted. In the preferred embodiment, the method includes the additional step of displaying the patient's compliance data and compliance status to the healthcare provider.

A preferred system for implementing the method of the invention includes a program display unit for displaying an entertainment program to the patient. The system also includes a monitoring device for collecting patient compliance data and a memory for storing the compliance evaluation criteria. An evaluation program compares the compliance data to the evaluation criteria to determine if the patient is in compliance with the treatment plan. The system further includes an access control device in communication with the evaluation program for controlling access to the entertainment program in dependence upon the compliance status of the patient.

BRIEF DESCRIPTION OF THE DRAWINGS

FIG. 2 is a sample evaluation criteria entry screen.

FIG. 5 is a sample compliance questions script according to the invention.

DESCRIPTION

The present invention is a system and method for controlling patient access to an entertainment program to encourage a patient to comply with a treatment plan. In the following detailed description, numerous specific details are set forth in order to provide a thorough understanding of the present invention. However, it will be apparent to one of ordinary skill in the art that these specific details need not be used to practice the invention. In other instances, well known structures, interfaces, and processes are not shown in detail to avoid unnecessarily obscuring the present invention.

Figure 1:
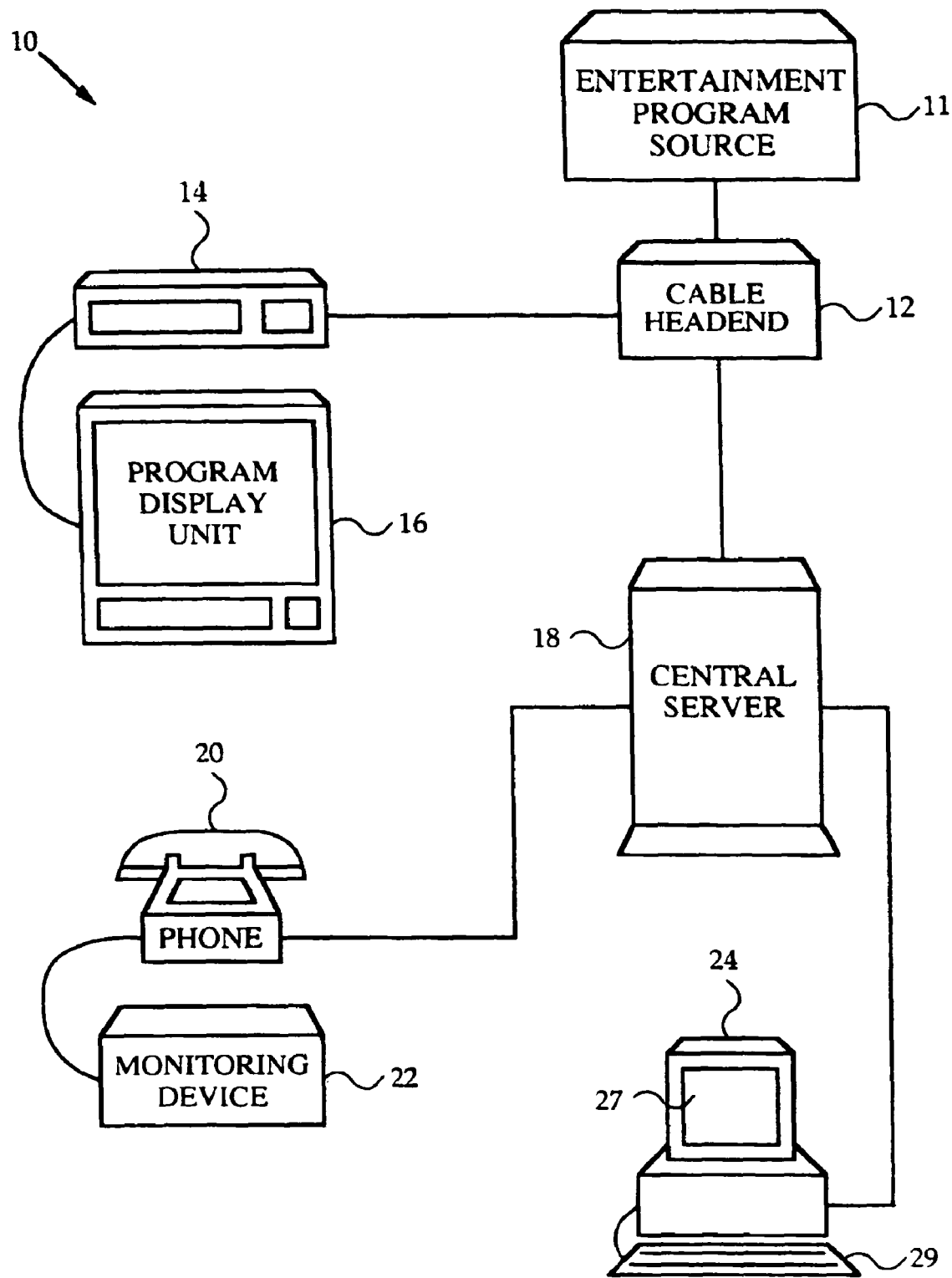
FIG. 1 is a schematic block diagram of an access control system according to the invention.

A preferred embodiment of the invention is illustrated in FIGS. 1-9. FIG. 1 is a schematic block diagram of an access control system 10 for controlling patient access to an entertainment program. The system includes an entertainment program source 11 for broadcasting the entertainment program to a local cable operator headend 12. In the preferred embodiment, program source 11 is a satellite television broadcast system and the entertainment program is a television program. Headend 12 is connected via cable to a television set-top processor 14, in the preferred embodiment a cable converter box.

Set-top processor 14 is connected to a program display unit, such as a television 16, for displaying the television program to the patient. Specific techniques for establishing a cable television system in this manner are well known in the art. Although set-top processor 14 is illustrated as a separate device in FIG. 1, those skilled in the art will appreciate that processor 14 may be built into the television or built into a video cassette recorder.

A central server 18 of a healthcare clinic is connected to headend 12 such that server 18 is in communication with set-top processor 14 through headend 12. A DTMF telephone 20 is connected to server 18 via standard telephone lines. Telephone 20 is for collecting patient answers to compliance questions through an automated telephone call, as will be explained below. A medical monitoring device 22 is connected to telephone 20 such that monitoring device 22 is in signal communication with server 18 through telephone 20.

Monitoring device 22 is capable of producing measurements of a physiological condition of the patient and recording the measurements for later transmission to server 18. For example, for a diabetic patient, device 22 is a blood glucose meter for measuring the patient's blood glucose levels. For an asthmatic patient, device 22 is a peak flow meter for measuring the patient's peak flow rates. Such monitoring devices for recording and transmitting measurements are well known in the art. Further, those skilled in the art will appreciate that monitoring device 22 need not be connected to server 18 through telephone 22. For example, in an alternative embodiment, monitoring device 22 is a wireless device having an RF transmitter for transmitting the measurements to server 18 through an RF link. In another embodiment, device 22 is connected to server 18 through a separate modem connection.

A workstation 24 of a healthcare provider is networked to central server 18. Workstation 24 is preferably a personal computer or network terminal and includes a display 27 and a selection device 29, such as a mouse or keyboard. Workstation 24 is for entering in server 18 a treatment plan specification including compliance evaluation criteria for evaluating a compliance of the patient with the treatment plan.

FIG. 2 illustrates a treatment plan specification screen 31 as it appears on display 27 of workstation 24. Screen 31 includes a patient field 26 for specifying a patient to be evaluated and a disease field 28 for specifying the patient's disease. The preferred embodiment will be described with reference to a patient who has diabetes, although it is to be understood that the system may be used with patients having any type of health condition which requires a treatment plan.

Screen 31 includes check boxes 30 for selecting desired monitoring types. The monitoring types determine how the compliance of the patient with the treatment plan is to be monitored. For example, a diabetic patient may be monitored through a blood glucose meter, interactive telephone questions, on-screen questions, or an interactive educational program. This list of monitoring types represents a sample of the presently preferred monitoring types and is not intended to limit the scope of the access control system.

Screen 31 also includes check boxes 32 for selecting evaluation criteria corresponding to each monitoring type and data fields 34 for specifying criteria values. For example, FIG. 2 illustrates that the healthcare provider has selected glucose monitoring for the patient. The healthcare provider has also specified minimum glucose values, maximum glucose values, and a minimum number of glucose measurements the patient must make to comply with the treatment plan. The healthcare provider has further specified telephone question monitoring for the patient and a minimum score to be achieved by the patient in answering the questions. Screen 31 further includes a monitoring interval field 36 for specifying a desired monitoring interval, an OK button 38 for confirming the information entered in screen 31, and a CANCEL button 40 for canceling the information entered in screen 31.

Figure 3:
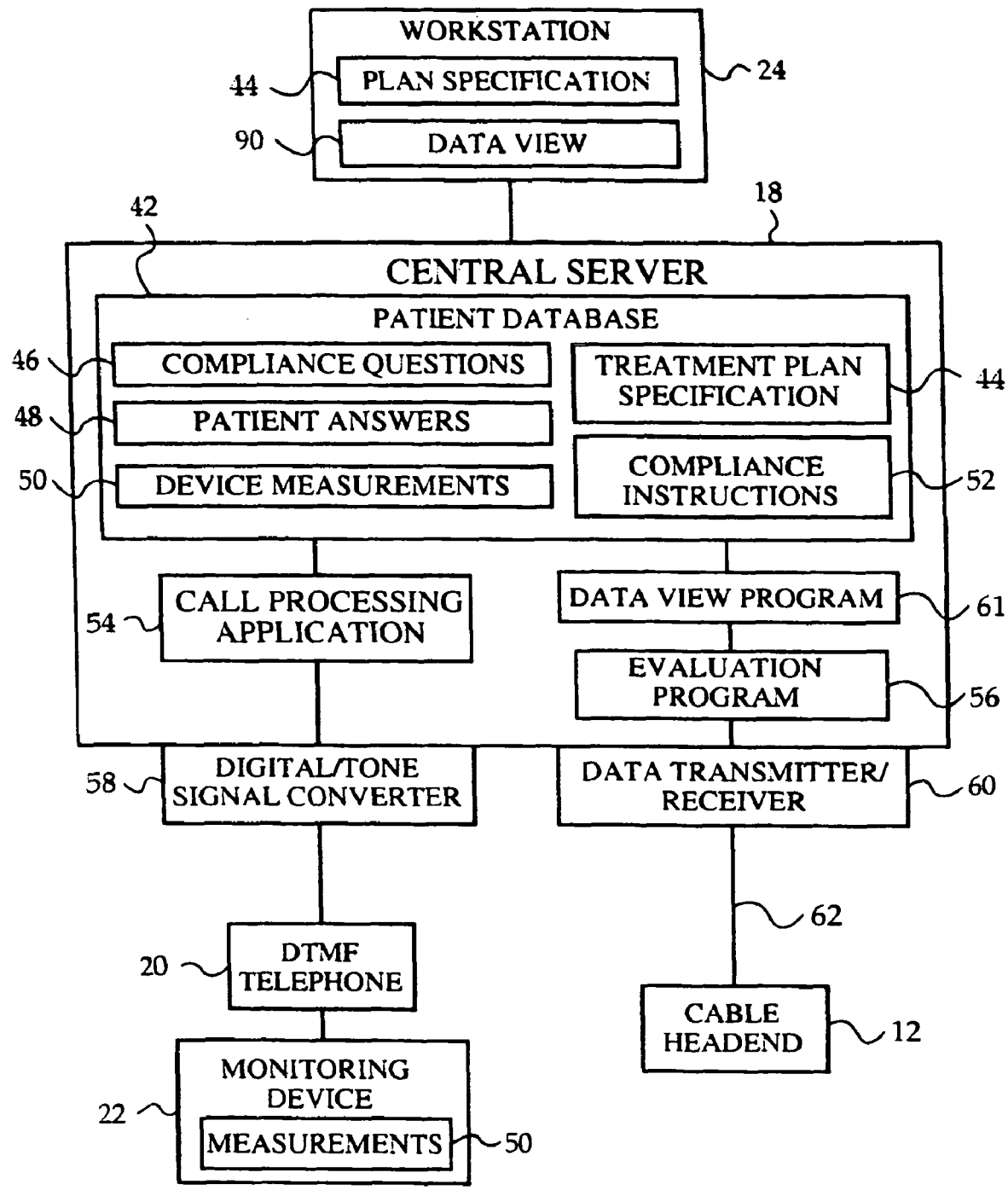
FIG. 3 is a schematic block diagram of a central server of the access control system of FIG. 1.

FIG. 3 is a schematic block diagram illustrating server 18 in greater detail. Server 18 has a patient database 42 for storing plan specification 44 received from workstation 24 and measurements 50 received from device 22. Database 42 is further capable of storing compliance questions 46, patient answers 48, and compliance instructions 52. Server 18 includes a call processing application 54 for placing an automated telephone call to the patient. Application 54 is designed to ask compliance questions 46 and receive patient answers 48 through telephone 20 and digital/tone signal converter 58. A compliance questions script 82 containing sample compliance questions is shown in FIG. 5. The programming of an automated call processing application to perform these functions is well known in the art.

Figure 9:
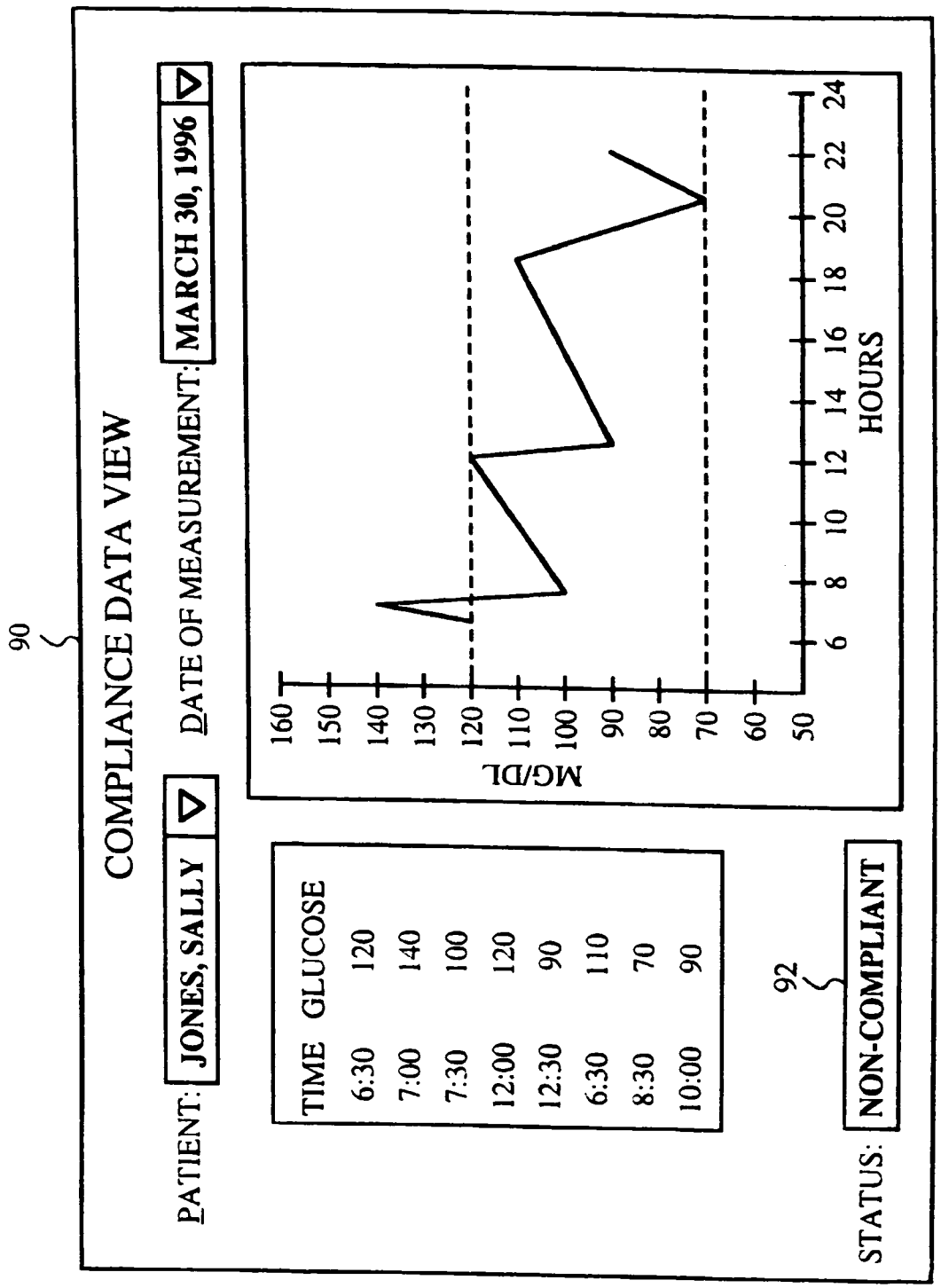
FIG. 9 is a sample compliance data view appearing on the screen of a provider workstation of the access control system of FIG. 1.

Server 18 further includes a data view program 61. Data view program 61 is designed to display device measurements 50 and a compliance status of the patient on the display of workstation 24. FIG. 9 shows a sample data view 90 produced by the data view program illustrating a diabetic patient's compliance data. Data view 90 includes a graph of the device measurements, as well as a compliance status field 92 indicating the current compliance status of the patient. Specific techniques for creating a data view program to display data in this manner are well known in the art.

Referring again to FIG. 3, server 18 additionally includes an evaluation program 56. Evaluation program 56 is designed to compare the compliance data received in database 42 to the evaluation criteria specified in plan specification 44 to determine a compliance status of the patient. Evaluation program 56 also includes program logic for performing various control functions described in the operation section below. Specific techniques for creating an evaluation program to perform the control functions described are well known in the art.

Server 18 is connected to a data transmitter/receiver 60 for transmitting data to headend 12 and receiving data from headend 12 through a data link 62. It will be apparent to one skilled in the art that data link 62 may comprise a telephone line, radio signal link, satellite link, or any other suitable link for transmitting data between a server and a cable headend.

Figure 4:
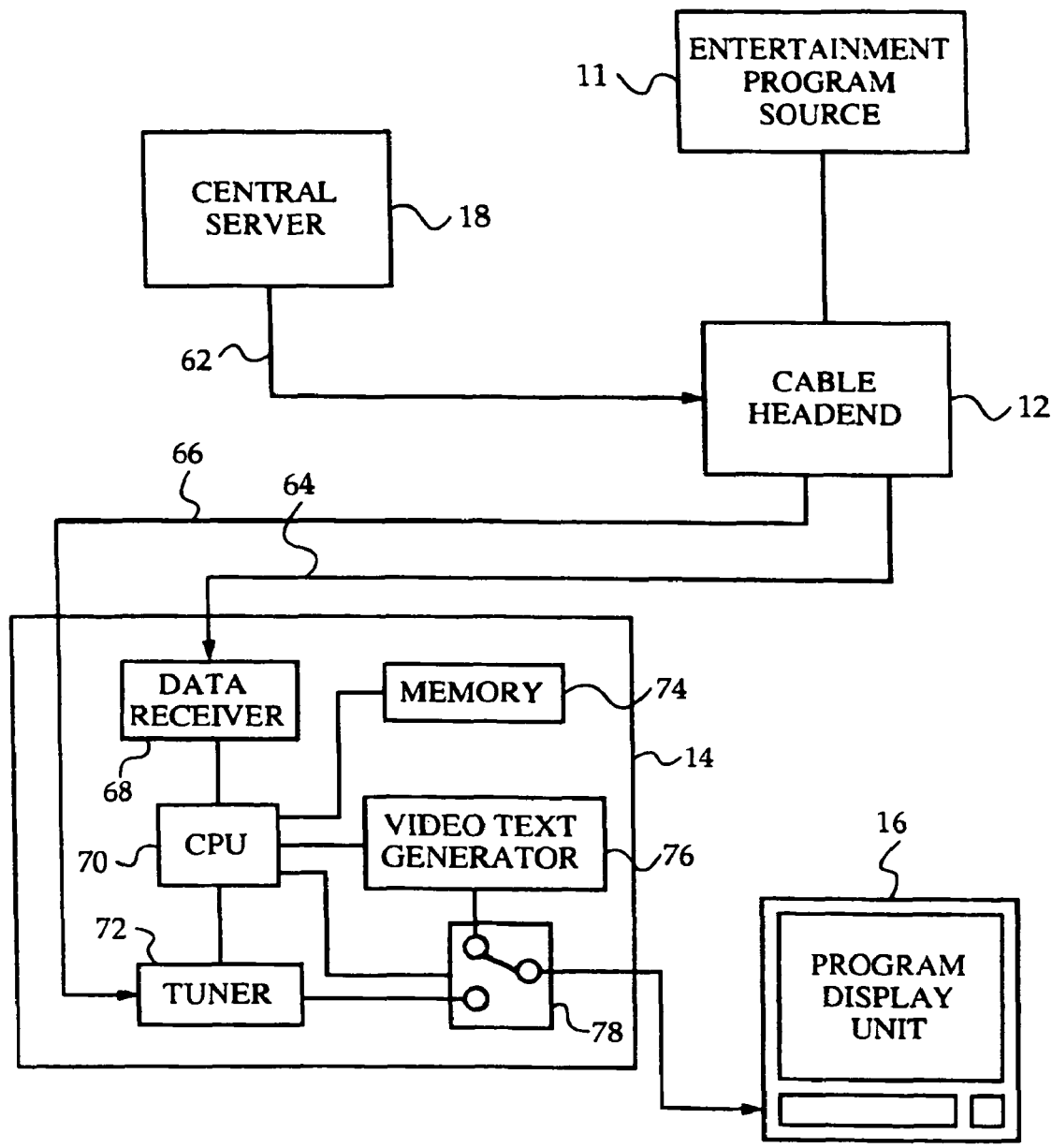
FIG. 4 is a schematic block diagram of an access control device of the access control system of FIG. 1.

FIG. 4 is a schematic block diagram illustrating the interaction of headend 12, set-top processor 14, and television 16 in greater detail. Headend 12 is designed to receive television program signals from program source 11 and relay the program signals to set-top processor 14 through a signal path 66. Headend 12 is further designed to receive data signals from server 12 through link 62 and relay the data signals to set-top processor 14 through a signal path 64. It will be apparent to one skilled in the art that signal paths 64 and 66 may be located in the same transmission cable connecting set-top processor 14 to headend 12.

Figure 6:
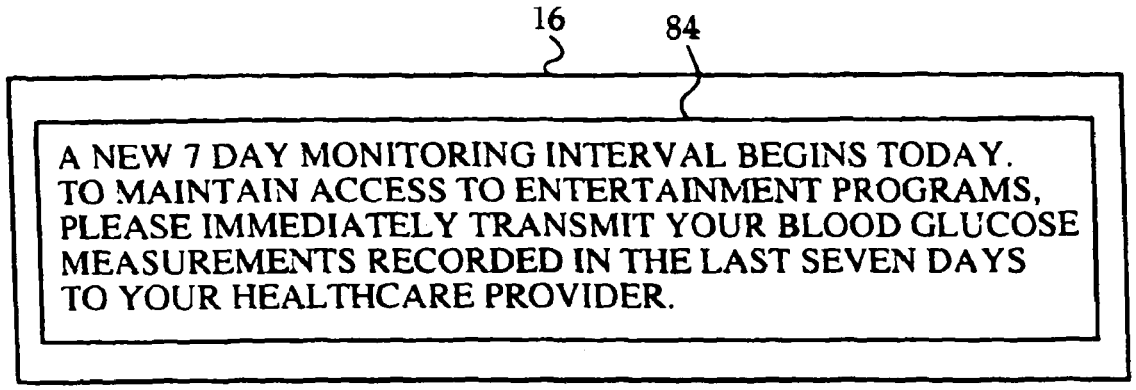
FIGS. 6-8 are sample messages appearing on the screen of a program display unit of the access control system of FIG. 1.
Figure 7:
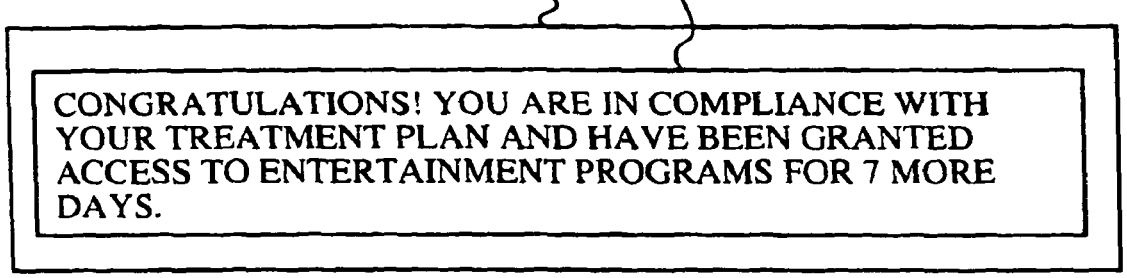
Figure 8:
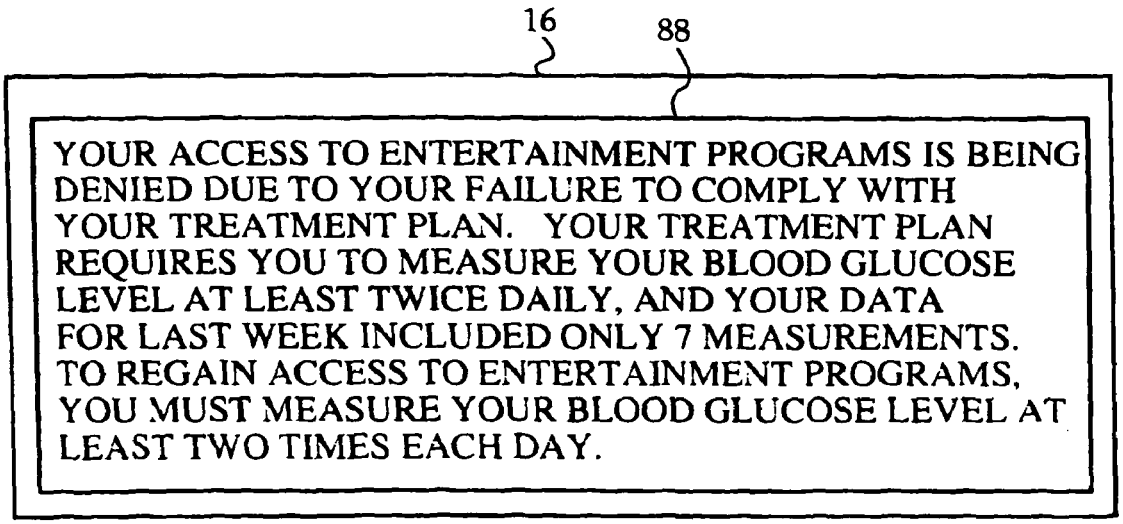

Set-top processor 14 has a television tuner 72 for receiving the television program signals from signal path 66. Set-top processor 14 also has a data receiver 68 for receiving the data signals from signal path 64 and for relaying the data signals to a microprocessor 70. A memory 74 and a video text generator 76 are connected to microprocessor 70. Set-top processor 14 also includes a switch 78 controlled by microprocessor 70. The switch has a first position for connecting generator 76 to television 16 and a second position for connecting tuner 72 to television 16. Generator 76 is designed to generate text messages for display on television 16. Sample text messages are shown in FIGS. 6-8 and will be explained in detail below.

Figure 10:
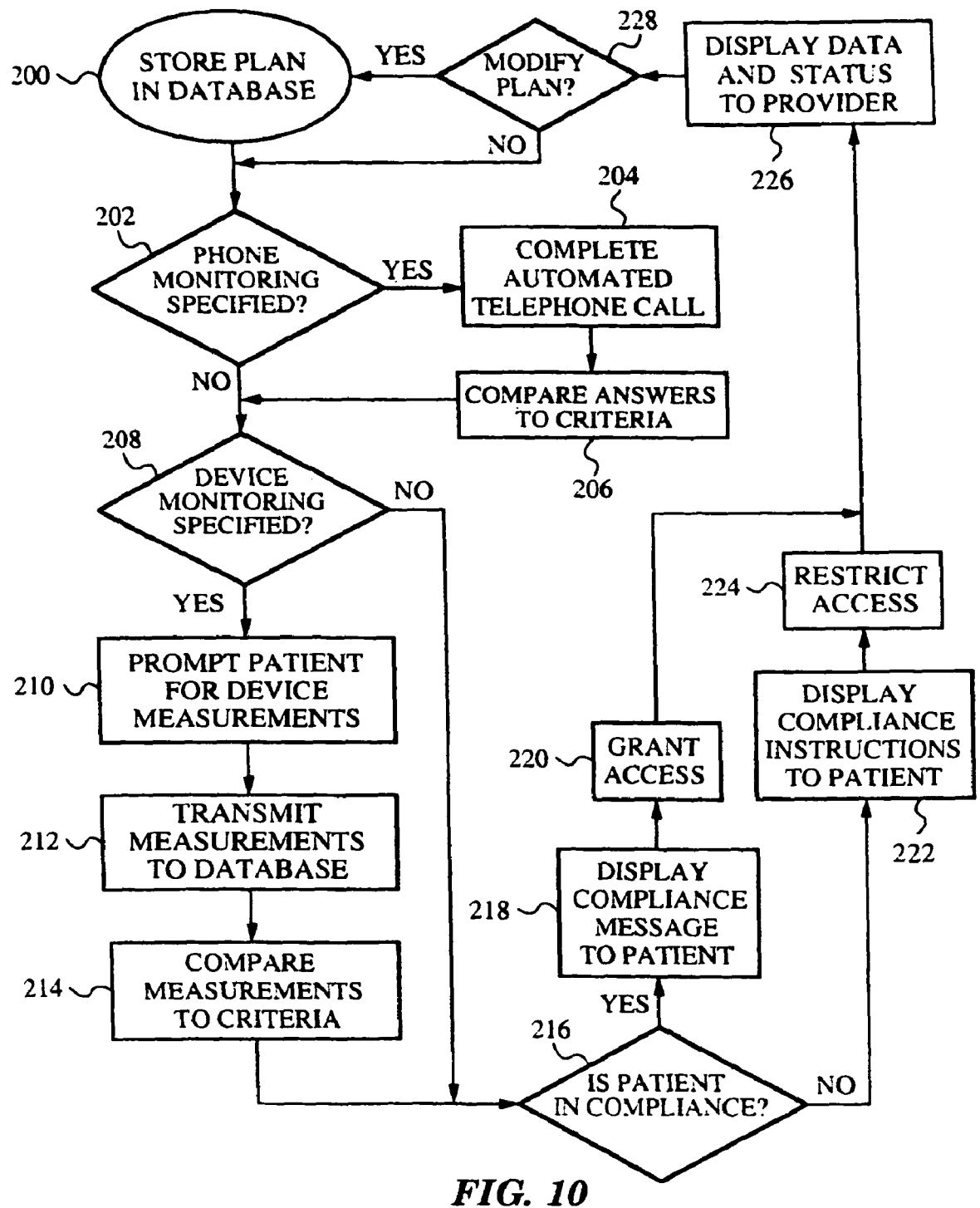
FIG. 10 is a flow chart illustrating steps included in a method of the invention.

The operation of the preferred embodiment is illustrated in FIG. 10. FIG. 10 is a flow chart showing a preferred method of using access control system 10 to encourage the patient to comply with the treatment plan. In step 200, plan specification 44 is selected by a healthcare provider and stored in database 42. The healthcare provider stores plan specification 44 including the selected evaluation criteria in database 42 by completing screen 31 on workstation 24 and pressing OK button 38, as shown in FIG. 2.

Next, evaluation program 56 determines if the healthcare provider specified telephone monitoring for the patient, decision step 202. If telephone monitoring is not specified, evaluation program 56 proceeds to decision step 208. If telephone monitoring is specified, call processing application 54 completes an automated telephone call to the patient, step 204. Call processing application 54 places the call to the patient through telephone 20 and asks compliance questions 46. The patient answers the questions using the touch tone key pad of telephone 20. Patient answers 48 are received through converter 58 and stored in database 42. Next, evaluation program 56 compares patient answers 48 to the evaluation criteria specified in plan specification 44, step 206.

As shown in FIG. 2, the healthcare provider specified that the compliance questions need only be completed by the patient to be in compliance. In an alternative embodiment, the healthcare provider may enter a minimum numeric score the patient must achieve to be in compliance. In this embodiment, the evaluation program includes program logic for scoring the patient answers and for comparing the patient's score to the minimum score specified by the healthcare provider.

The advantage of merely requiring the patient to provide complete answers to the compliance questions is that it removes the temptation for the patient to be untruthful in his or her answers in an effort to achieve a false compliance status. It is a significant advance in healthcare to motivate a patient to supply information to a healthcare provider on a regular basis, even if the information indicates that the patient is having difficulty with the treatment plan. Thus, in the preferred embodiment, the patient is deemed to be in compliance if the patient provides complete answers to the compliance questions.

Following step 206, evaluation program 56 proceeds to decision step 208, determining if the healthcare provider specified device monitoring for the patient. If device monitoring is not specified, evaluation program 56 proceeds to decision step 216. If device monitoring is specified, evaluation program 56 proceeds to step 210, prompting the patient to transmit measurements 50 to server 18.

To prompt the patient, server 18 transmits prompt signals to set-top processor 14 through link 62 and path 64, as shown in FIG. 4. The prompt signals include prompt data used by text generator 76 to generate a prompting message on television 16. Microprocessor 70 places switch 78 in its first position to connect text generator 76 to television 16. Generator 76 then produces a prompt message 84 which is displayed on television 16, as shown in FIG. 6.

Upon reading the prompt, the patient transmits measurements 50 from monitoring device 22 to central server 18, step 212, and the measurements are stored in database 42. Evaluation program 56 then compares the measurements to the criteria values specified by the healthcare provider, step 214. In step 216, evaluation program 56 determine a compliance status of the patient based on the comparison of measurements 50 and patient answers 48 to the corresponding criteria values specified by the healthcare provider. If the patient is in compliance, a compliance message is displayed to the patient, step 218, and access is granted to the television program, step 220.

To display the compliance message and grant access to the television program, server 18 transmits compliance message signals and a grant access control signal to set-top processor 14 through link 62 and path 64, as illustrated in FIG. 4. The compliance message signals include compliance message data used by text generator 76 to generate the compliance message on television 16. Microprocessor 70 places switch 78 in its first position to connect text generator 76 to television 16. Generator 76 then produces a compliance message 86 which is displayed on television 16, as shown in FIG. 7. The grant access control signal instructs microprocessor 70 to place switch 78 in its second position following the display of message 86. In its second position, switch 78 connects tuner 72 to television 16 so that the patient has access to the television program.

If the patient is not in compliance, an instructional message is displayed to the patient, step 222, and access is restricted to the television program, step 224. To display the instructional message and restrict access to the television program, server 18 transmits instruction signals and a restrict access control signal to set-top processor 14. The instruction signals include instructional message data used by text generator 76 to generate the instructional message on television 16. Microprocessor 70 places switch 78 in its first position to connect text generator 76 to television 16. Generator 76 then produces the instructional message which is displayed on television 16.

FIG. 8 shows a sample instructional message 88 as it appears on television 16. Message 88 contains an explanation of why access to the entertainment program is being restricted and compliance instructions which include a description of an action the patient must perform to satisfy the evaluation criteria. The restrict access control signal instructs microprocessor 70 to maintain switch 78 in its first position following the display of message 88. In its first position, switch 78 disconnects tuner 72 from television 16 so that the patient is denied access to the television program.

In step 226, the compliance data and compliance status of the patient are displayed to the healthcare provider in compliance data view 90, as shown in FIG. 9. Next, the health care provider determines if he or she wishes to modify the patient's treatment plan specification, decision step 228. If the healthcare provider desires to modify the plan specification, he or she returns to step 200, storing the plan specification in the database. If the healthcare provider does not desire to modify the plan specification, evaluation program 56 returns to step 202 and continues the monitoring loop at the specified monitoring interval.

Figure 11:
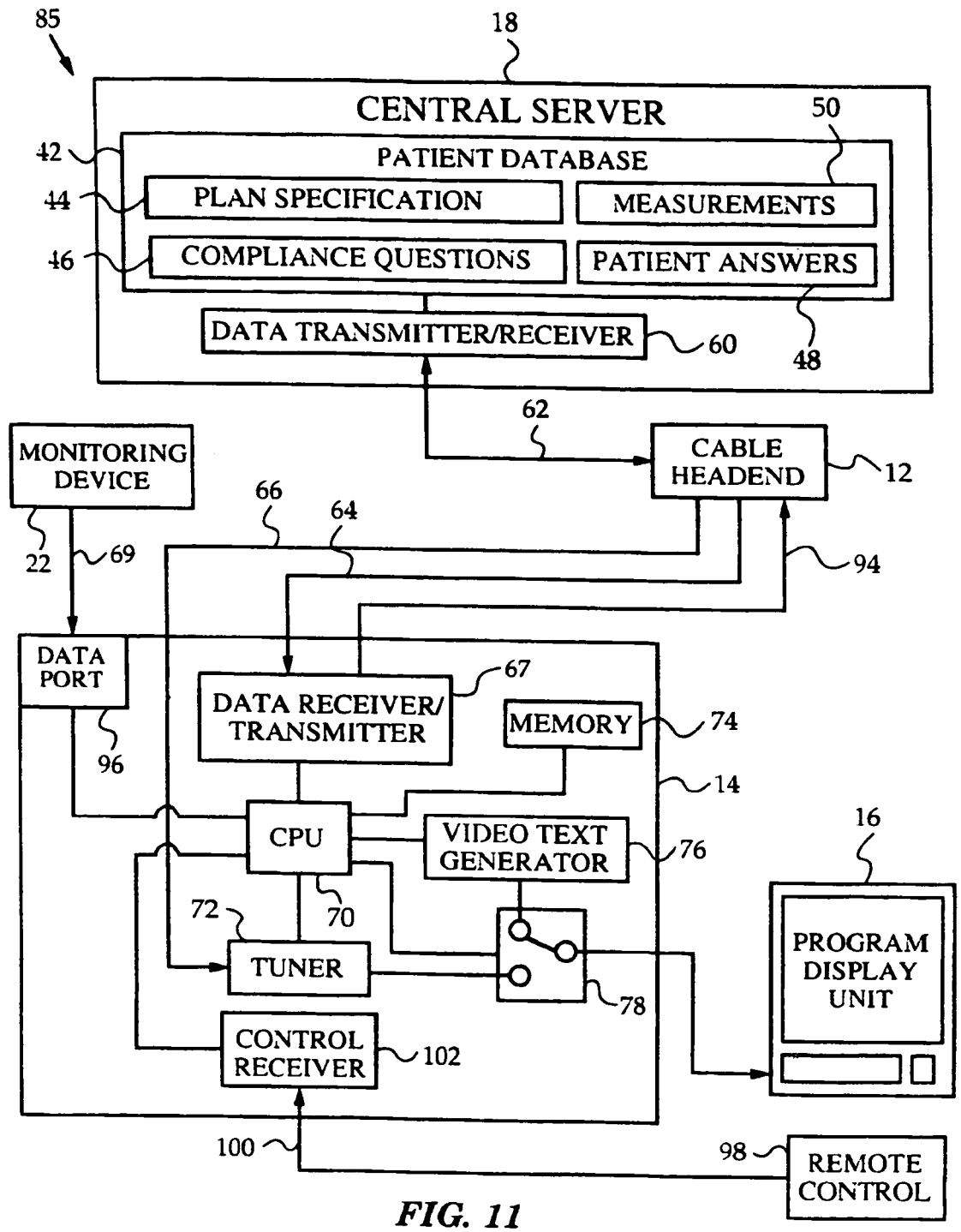
FIG. 11 is a schematic block diagram of another access control system according to the invention.
Figure 12:
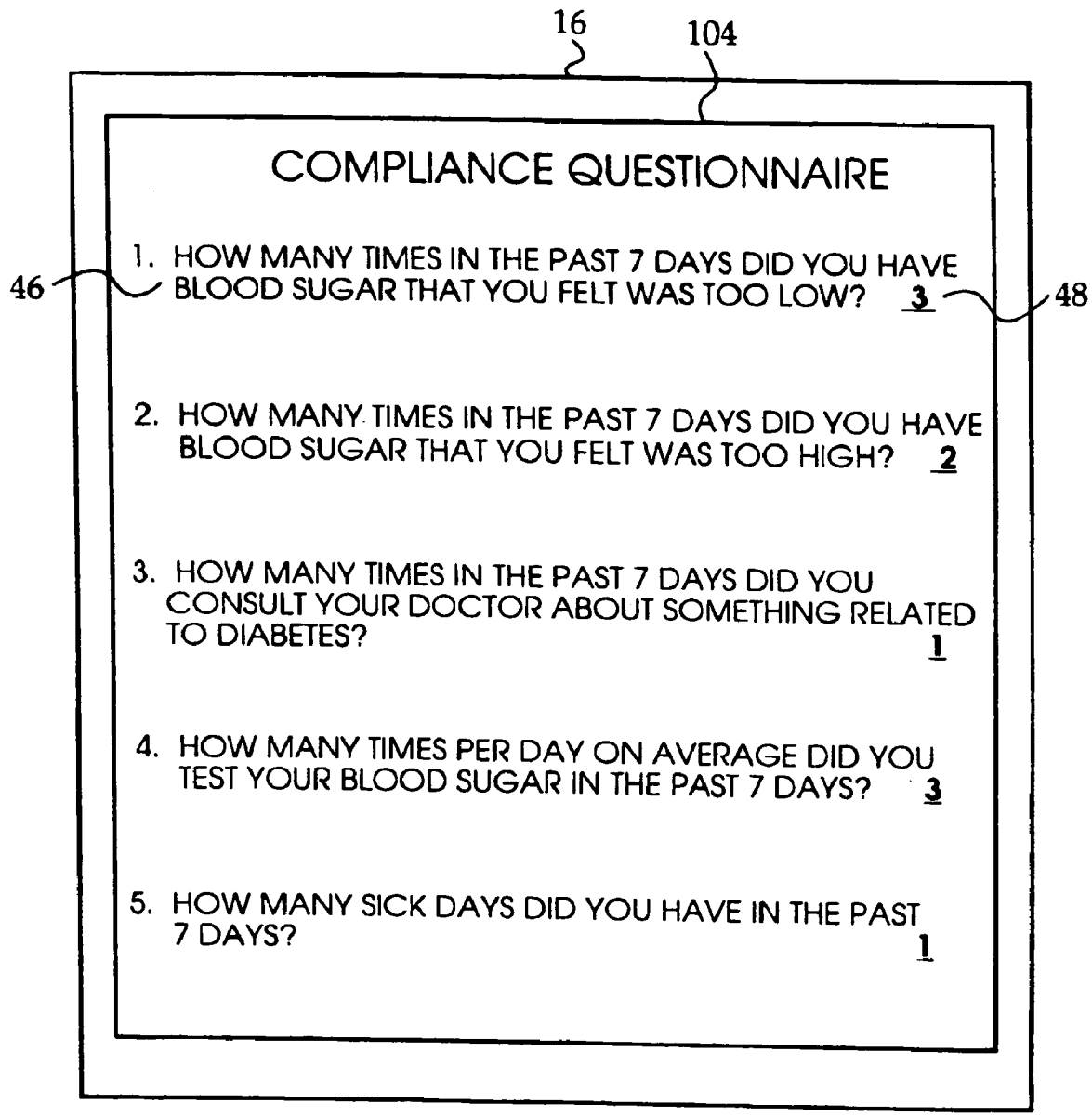
FIG. 12 is a sample compliance questionnaire appearing on the screen of a program display unit of the access control system of FIG. 11.

FIGS. 11-12 illustrate a second embodiment of the invention. The second embodiment differs from the preferred embodiment in that the evaluation program is stored and executed in the set-top processor rather than the server. Thus, in the second embodiment, the compliance status of the patient is determined by the set-top processor rather than the server.

Referring to FIG. 11, an access control system 85 includes a set-top processor 14 having a microprocessor 70 and a memory 74. Memory 74 stores the evaluation program to be executed by microprocessor 70 to determine a compliance status of the patient and to perform the control functions described in the operation section below. The programming of a microprocessor to perform the functions described is well known in the art. Memory 74 further stores compliance instructions for the patient and prompt data used by text generator 76 to produce prompting messages for display on television 16.

The second embodiment also differs from the preferred embodiment in that the patient is asked compliance questions through television 16 rather than through an automated telephone call. System 85 includes a user input device, such as remote control 98, for entering patient answers to the compliance questions. Remote control 98 is preferably a standard infrared remote for generating infrared signals 100. Set-top processor 14 has a control receiver 102 connected to microprocessor 70 for receiving infrared signals 100 from remote control 98.

The second embodiment further differs from the preferred embodiment in that monitoring device 22 is connected to set-top processor 14 rather than server 18. Set-top processor 14 has a data port 96 connected to memory 74 through microprocessor 70. Device 22 is connected to data port 96 through a connection cord 69 such that measurements 50 may be uploaded to microprocessor 70 for storage in memory 74. Set-top processor 14 further includes a data receiver/transmitter 67 for receiving data input signals from headend 12 through signal path 64 and for transmitting data output signals to headend 12 through a signal path 94. Signal paths 64 and 94 are preferably located in the same transmission cable connecting set-top processor 14 to headend 12.

Figure 13:
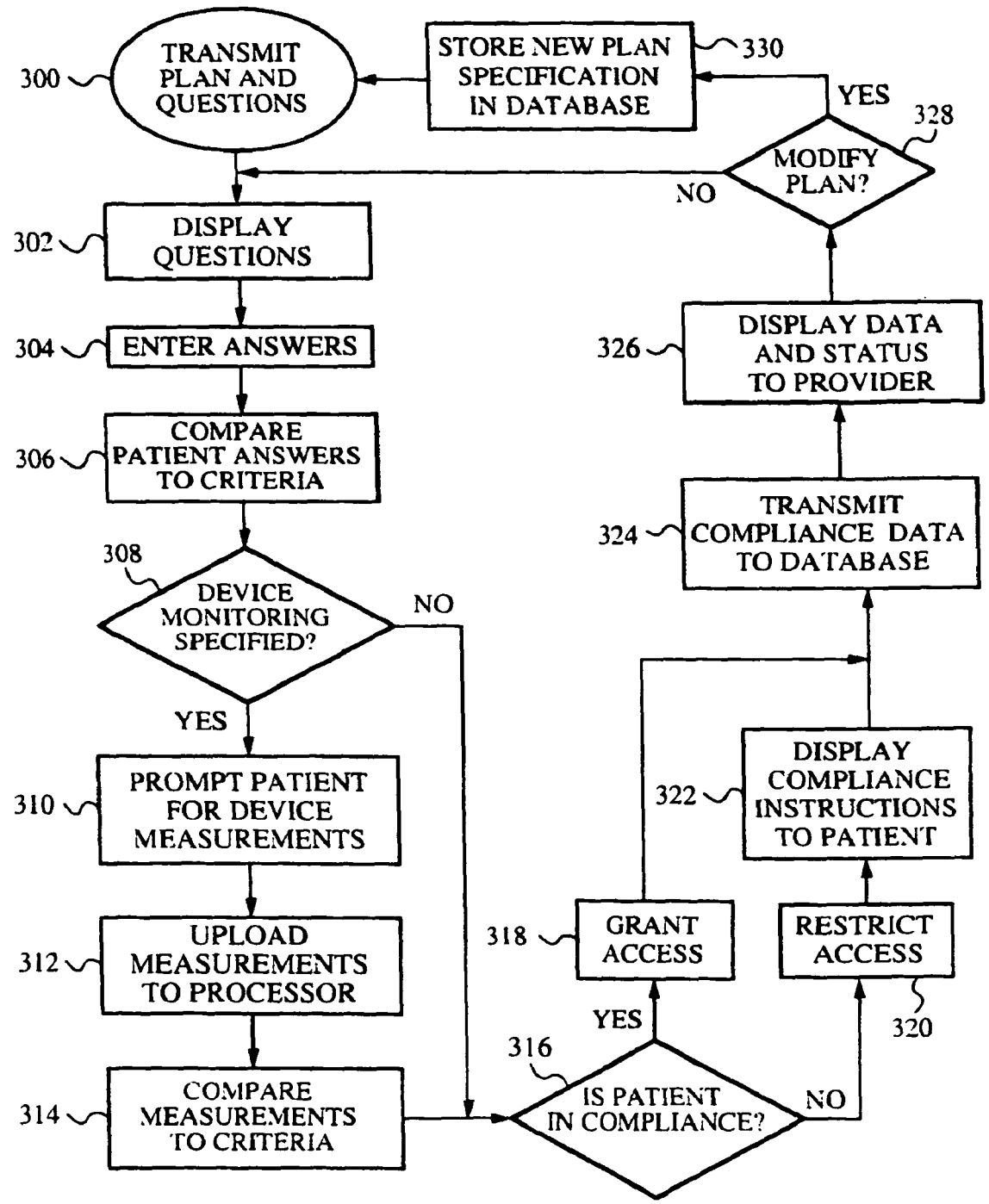
FIG. 13 is a flow chart illustrating steps included in another method of the invention.

The operation of the second embodiment is shown in FIG. 13. FIG. 13 is a flow chart showing a preferred method of using access control system 85 to encourage a patient to comply with a treatment plan. In step 300, plan specification 44 and compliance questions 46 are transmitted from server 18 to set-top processor 14 through link 62 and signal path 64. Plan specification 44 and compliance questions 46 are received by receiver/transmitter 67 and stored in memory 74. In step 302, text generator 76 produces a compliance questionnaire which is displayed to the patient on television 16. FIG. 12 illustrates a sample compliance questionnaire 104 containing compliance questions 46.

The patient enters answers 48 to compliance questions 46 using remote control 98, step 304. The patient answers are received through control receiver 102 and stored in memory 74. Microprocessor 70 compares the patient answers to the criteria specified in plan specification 44, step 306. Next, microprocessor 70 determines if plan specification 44 specifies device monitoring for the patient, decision step 308. If device monitoring is not specified, microprocessor 70 proceeds to decision step 316. If device monitoring is specified, microprocessor 70 proceeds to step 310, prompting the patient to upload device measurements 50 to set-top processor 14.

To prompt the patient, text generator 76 generates a prompt message which is displayed on television 16 asking the patient to upload measurements 50 to set-top processor 14. The patient then uploads the measurements from monitoring device 22 to set-top processor 14 through cord 69, step 312. The measurements are received through data port 96 and stored in memory 74.

In step 314, microprocessor 70 compares the measurements to the criteria values specified in plan specification 44. In step 316, microprocessor 70 determines a compliance status of the patient based on the comparison of measurements 50 and patient answers 48 to the corresponding criteria values specified in plan specification 44, decision step 316. If the patient is in compliance, access is granted to the desired television program, step 318. To grant access, microprocessor 70 positions switch 78 in its second position to connect tuner 72 to television 16. Microprocessor 70 then proceeds to step 324.

If the patient is not in compliance, access is restricted to the television program, step 320, and the compliance instructions are displayed to the patient on television 16, step 324. To restrict access to the television program and display the compliance instructions, microprocessor 70 places switch 78 in its first position to connect text generator 76 to television 16.

Generator 76 then produces an instructional message which is displayed on television 16. As described in the preferred embodiment above, the message contains an explanation of why access to the entertainment program is being restricted and compliance instructions which include a description of an action the patient must perform to satisfy the evaluation criteria. Microprocessor 70 maintains switch 78 in its first position following the display of the message so that the patient is denied access to the television program.

In step 324, the device measurements, patient answers, and compliance status of the patient are transmitted from set-top processor 14 to server 18 through signal path 94 and link 62. The compliance status, measurements, and patient answers are stored in database 42. The remaining operation of the second embodiment is analogous to the operation of the preferred embodiment described above.

Although the second embodiment has been described with the central server communicating with the set-top processor through the cable headend, it is obvious that the central server could also be connected directly to the set-top processor through telephone lines, or a similarly suitable network connection. Communication through the cable headend is presently preferred so that the set-top processor need only have one network connection, but it is anticipated that the central server may be in direct communication with the set-top processor.

Figure 14:
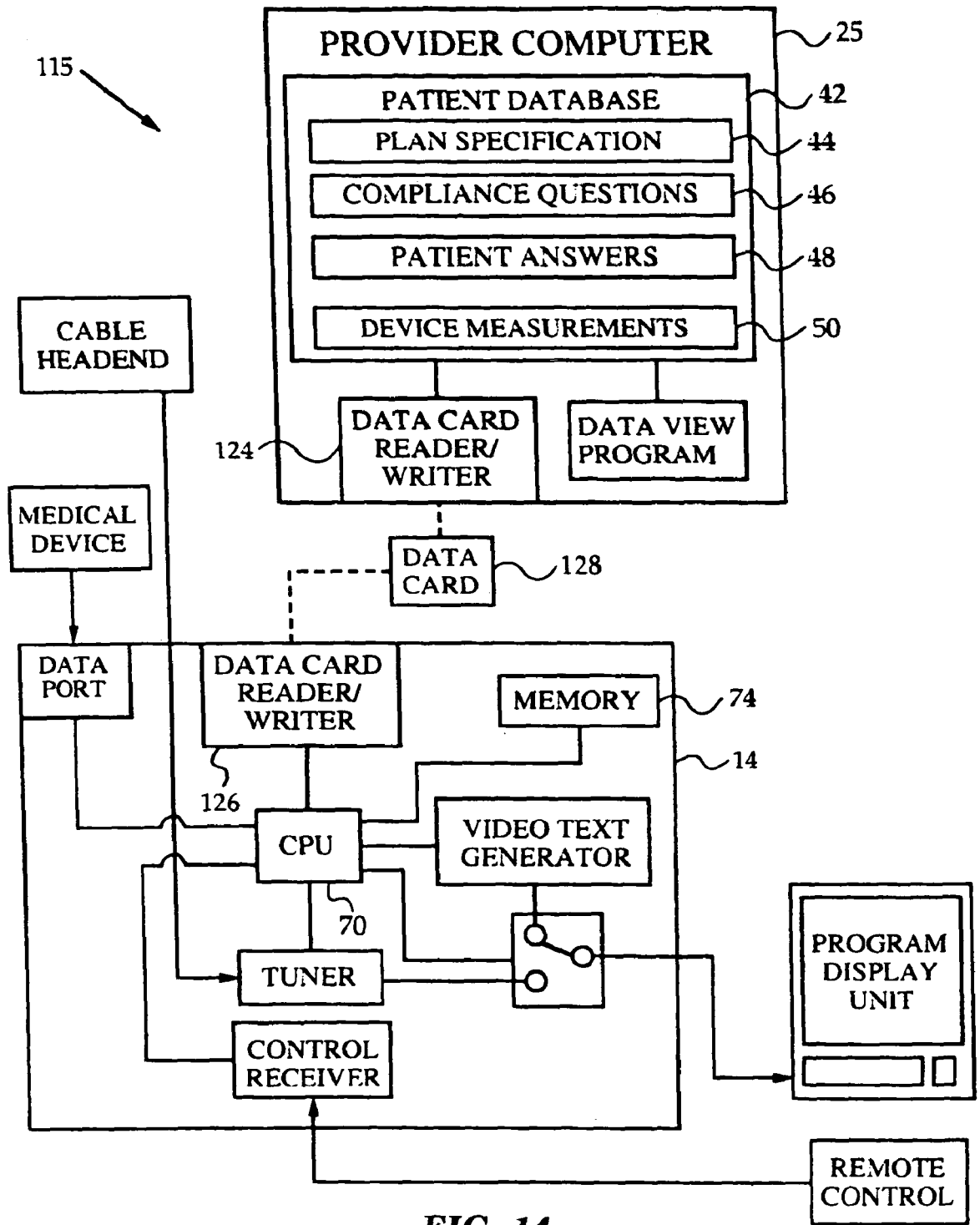
FIG. 14 is a schematic block diagram of another access control system according to the invention.

FIG. 14 shows a third embodiment of the invention. The third embodiment is similar in design and operation to the second embodiment described above. However, the third embodiment differs from the second embodiment in that the central server and workstation are replaced by a single healthcare provider computer. The third embodiment also differs from the second embodiment in that data is transferred between the set-top processor and provider computer using a data storage card rather than network connections.

As shown in FIG. 14, an access control system 115 includes a healthcare provider computer 25, preferably a personal computer. Computer 25 includes patient database 42 for storing plan specification 44, compliance questions 46, patient answers 48, and device measurements 50. Computer 25 also includes a data card reader/writer 124 for receiving a data storage card 128, such as a smart card or computer disk. Reader/writer 24 is designed to read data from card 128 and write data to card 128. Set-top processor 14 has a corresponding card reader/writer 126 for reading data from card 128 and writing data to card 128.

The operation of the third embodiment is analogous to the operation of the second embodiment previously described with reference to FIG. 13. The operation of the third embodiment differs only in step 300, transmitting plan specification 44 and compliance questions 46 to set-top processor 14, and step 324, transmitting the compliance data to database 42. In the third embodiment, step 300 is performed by writing plan specification 44 and compliance questions 46 on card 128 using reader/writer 124 of provider computer 25. The healthcare provider typically performs this step during a patient office visit. The patient then takes card 128 to set-top processor 14 and inserts card 128 in reader/writer 126. Plan specification 44 and compliance questions 46 are then read and stored in memory 74.

Similarly, step 302 is performed by writing patient answers 48 and measurements 50 on card 128 using reader/writer 126 of set-top processor 14. The patient then takes card 128 to the healthcare provider. The healthcare provider inserts card 128 in reader/writer 124. Patient answers 48 and measurements 50 are then read and stored in database 42. Other than the differences described, the operation of the third embodiment is the same as the operation of the second embodiment described above.

Figure 15:
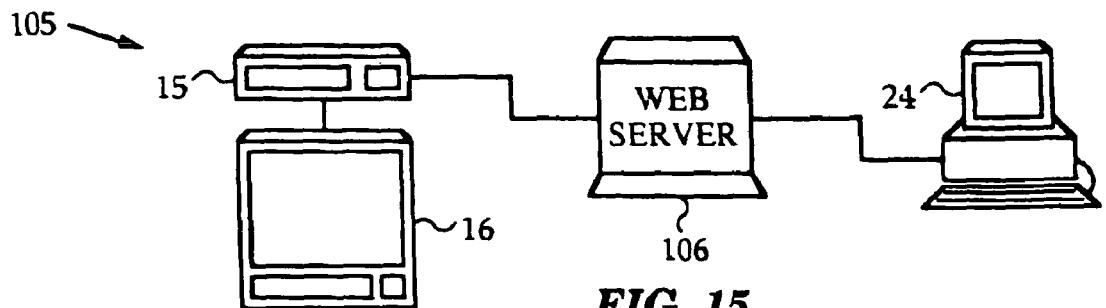
FIG. 15 is a schematic block diagram of another access control system according to the invention.
Figure 16:
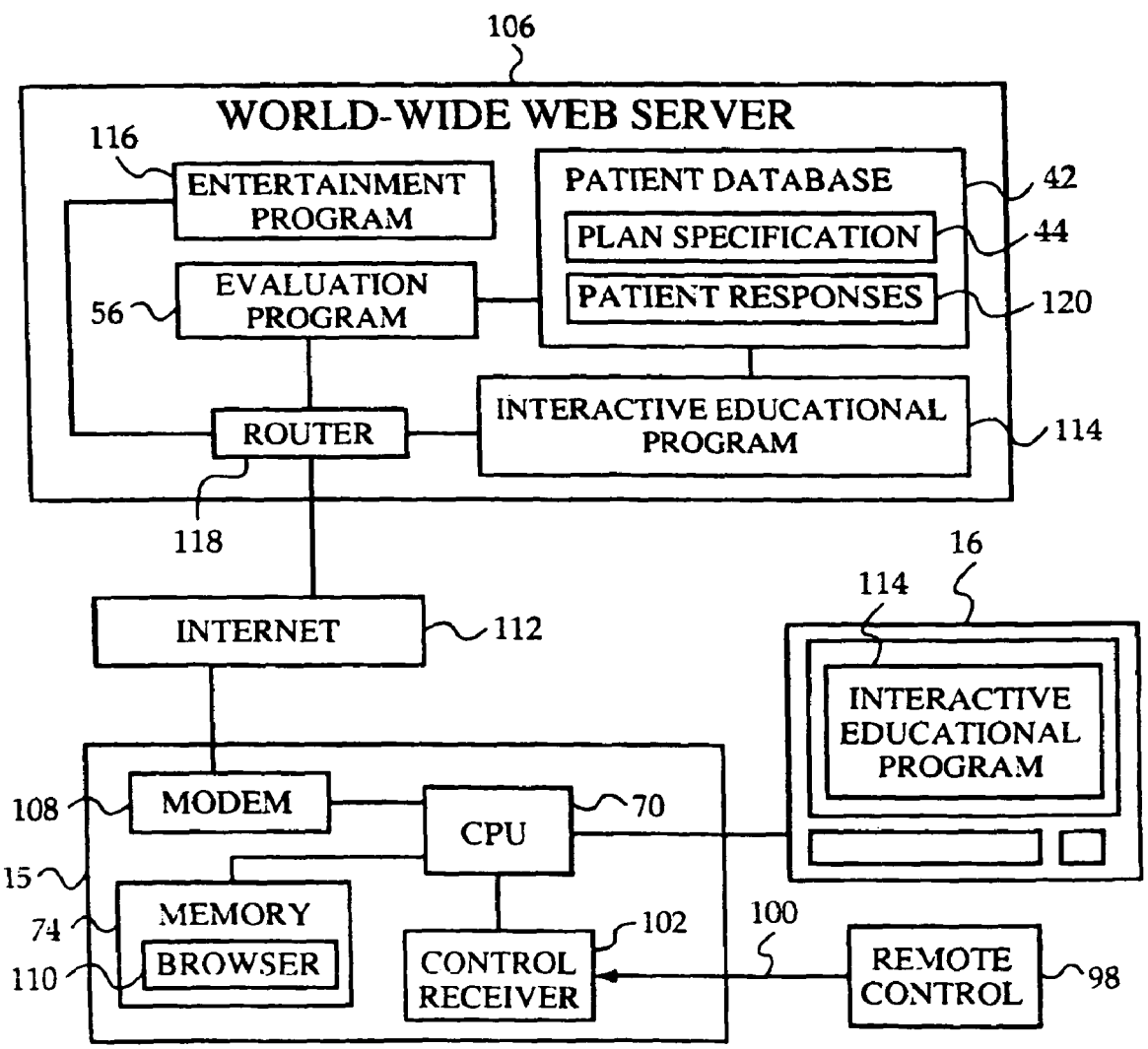
FIG. 16 is a schematic block diagram of a web server, television set-top processor, and program display unit of the access control system of FIG. 15.

A fourth embodiment of the invention is illustrated in FIGS. 15-16. The fourth embodiment differs from the preferred embodiment in that the entertainment program source is a world wide web server and the entertainment program is a web entertainment program. Referring to FIG. 15, an access control system 105 includes a web server 106 connected to a web television set-top processor 15. Set-top processor 15 is connected to television 16 such that television 16 displays to the patient world wide web programs accessed through set-top processor 15. Workstation 24 is networked to web server 106 for entering in web server 106 plan specification 44.

The fourth embodiment also differs from the preferred embodiment in that the compliance data collected from the patient includes patient responses to an interactive educational program. Referring to FIG. 16, web server 106 includes an interactive educational program 114 for teaching the patient proper treatment of his or her health condition and for asking the patient questions about the information presented. Such interactive educational programs for teaching a patient about a health condition are well known in the art. Web server 106 also includes a patient database 42 for storing plan specification 44 received from workstation 24 and patient responses 120 to program 114.

Web server 106 further includes a router 118 for routing patient access between educational program 114 and a web entertainment program 116. Web server 106 additionally includes evaluation program 56. In this embodiment, evaluation program 56 is designed to compare patient responses 120 received in database 42 to the evaluation criteria specified in plan specification 44 to determine a compliance status of the patient. Evaluation program 56 also includes program logic for performing various control functions described in the operation section below. Specific techniques for creating an evaluation program to perform the control functions described are well known in the art.

Set-top processor 15 includes a web browser program 110 stored in memory 74. Set-top processor 15 also includes a modem 108. Microprocessor 70 is connected to memory 74 and modem 108 to execute browser program 110 and access web server 106 through internet communication network 112. Set-top processor 15 also includes control receiver 102 connected to microprocessor 70 for receiving infrared signals 100 from remote control 98.

Figure 17:
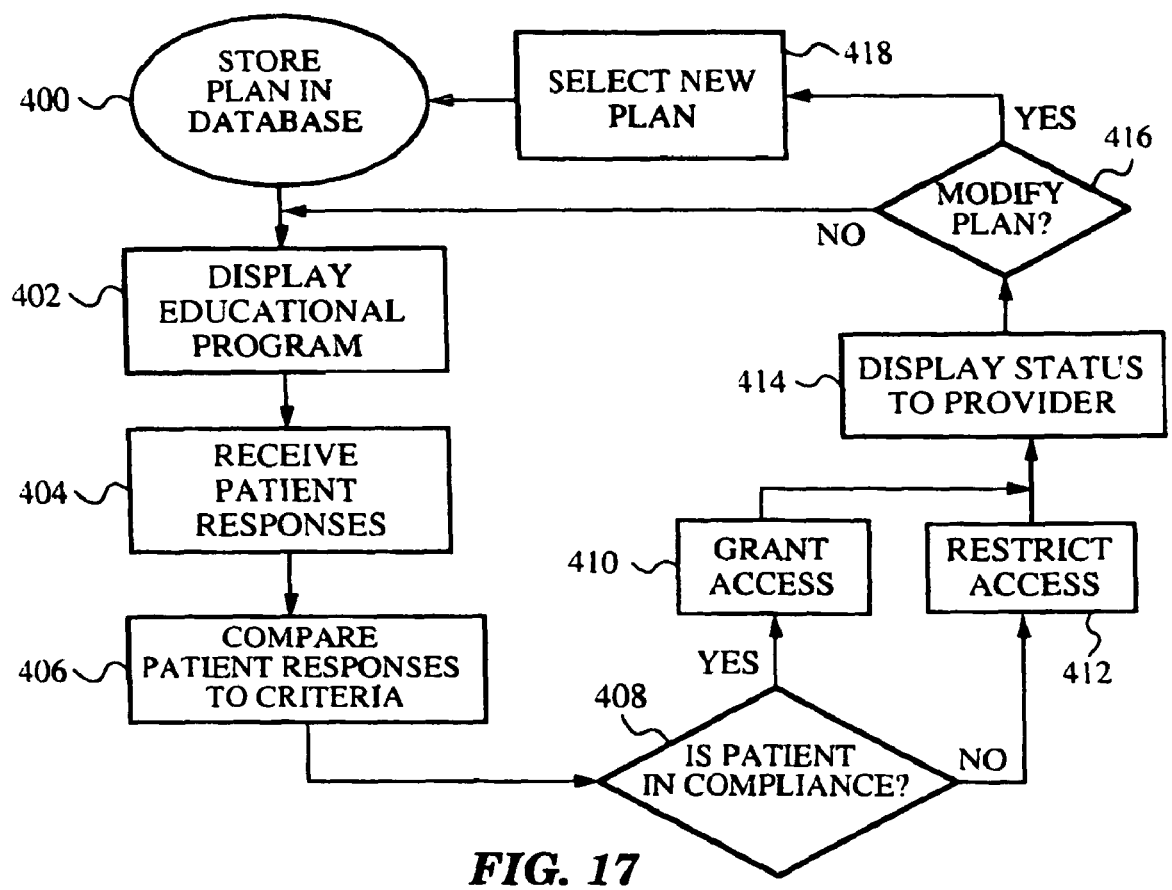
FIG. 17 is a flow chart illustrating steps included in another method of the invention.

The operation of the fourth embodiment is shown in FIG. 17. FIG. 17 is a flow chart showing a preferred method of using system 105 to control patient access to entertainment program 116. In step 400, plan specification 44 is stored in web server 106 through workstation 24. Next, the patient accesses web server 106 through set-top processor 15 and network 112. Router 118 initially routes the patient to educational program 114 and restricts access to entertainment program 116. Educational program 114 is displayed on television 16, step 402.

As the patient interacts with educational program 114, he or she enters patient responses 120 using remote control 98.

Patient responses 120 are received by web server 106 and stored in database 42, step 404. Next, evaluation program 56 compares the patient responses to the criteria specified in plan specification 44, step 406. Evaluation program 56 then determines if the patient is in compliance, decision step 408. If the patient is in compliance, access is granted to entertainment program 116, step 410. To grant access, evaluation program 56 instructs router 118 to route the patient to entertainment program 116.

If the patient is not in compliance, access is restricted to entertainment program 116, step 412. Router 118 continues to restrict the patient's access to entertainment program 116 until evaluation program 56 determines that the patient is in compliance. The remaining operation of the fourth embodiment is analogous to the operation of the preferred embodiment described above.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the invention is not limited to controlling patient access to a television program or world wide web program. The method of the invention is equally effective for controlling access to any entertainment program which may be broadcast or otherwise transmitted to consumers. In embodiments that control access to television programs, the invention is not limited to cable television systems. It is anticipated that the method of the invention will be used with direct broadcast satellite systems or any other system for broadcasting television programming.

Additionally, the set-top processor described is exemplary of just one possible embodiment of the invention. Those skilled in the art will appreciate that many other types of processors may be used to restrict access to an entertainment program. For example, an alternative embodiment includes a processor having a signal decoder which is selectively enabled and disabled by an entertainment broadcast company. In this embodiment, the broadcast company receives the patient's compliance status directly from the central server or healthcare provider and grants or restricts access to its broadcast entertainment programs by selectively enabling and disabling the processor.

Further, the preferred embodiment describes the use of medical monitoring devices and telephones for collecting compliance data from the patient. However, many other methods of collecting data from a patient are possible in alternative embodiments. For example, the patient could be provided with an electronic logbook and modem for transmitting compliance data via telephone lines. In another embodiment, the patient is provided with a paper based logbook and an automated reader for digitizing and transmitting the compliance data to the patient database. Alternatively, the patient could mail or fax the compliance data to the healthcare provider for entry into the database.

The compliance questions and compliance instructions illustrated are exemplary of just one possible embodiment of the invention. Many other questions and instructions may be displayed or telephoned to patients in alternative embodiments. Additionally, the preferred embodiment describes a system and method for encouraging patients having diabetes. However, the invention is not limited to diabetic patients. The system and method described are equally effective for patients having asthma, hypertension, cardiovascular disease, eating disorders, HIV, mental health disorders, or any other health condition requiring a treatment plan.

Therefore, the scope of the invention should be determined not by the examples given but by the appended claims and their legal equivalents.

What is claimed is:

1. A system for monitoring an individual, comprising:
    a server;
    a monitoring device in communication with said server, said monitoring device measures a health condition and vital signs of a user and transmits health condition information to said server, said monitoring device communicates with said server through a radio frequency link;
    a microprocessor based unit remotely located from said server and in communication with said server, said microprocessor based unit configured for receiving an entertainment program signal from a communicatively coupled entertainment program source;
    a display unit coupled to said microprocessor based unit; and
    a telephone in communication with said server, wherein said server communicates a first information to said user via said telephone, said first information includes a set of questions, said telephone receiving a second information from said user in response to said first information, said second information is feedback to said first information wherein said server receives said health condition information from said monitoring device and said second information within a single database, said server providing a grant access control signal to the microprocessor based unit when said second information is determined by said server as being in compliance with a pre-established compliance criteria for a prescribed medical treatment plan, said grant access control signal configured for causing the microprocessor based unit to allow user access to the entertainment program signal via the display unit, said server providing a restrict access control signal to the microprocessor based unit when said second information is determined by said server as not being in compliance with the pre-established compliance criteria for the prescribed medical treatment plan, said restrict access control signal configured for causing the microprocessor based unit to deny user access to the entertainment program signal via the display unit.

2. The system as claimed in claim 1, further comprising a computer remotely located from said server in communication with said server.

3. The system as claimed in claim 2, wherein said computer communicates said first information to said server.

4. The system as claimed in claim 1, wherein said first information includes a set of instructions.

5. The system as claimed in claim 1, wherein said server is a web server.

6. A method, executable by a microprocessor based unit, for acquiring health related information, said method comprising:
    presenting a web-based survey, said web-based survey including a graphical user interface that has at least one question related to a health condition provided in a textual format;
    receiving at least one response from a user to said web-based survey, said response being visible on said graphical user interface;
    providing health-related information based upon said at least one response;

receiving an entertainment program signal from a communicatively coupled entertainment program source;

determining compliance of said user with a pre-established compliance criteria for a prescribed medical treatment plan based upon said at least one response;

when said at least one response is determined as being in compliance with the pre-established compliance criteria for the prescribed medical treatment plan, providing a grant access control signal, said grant access control signal configured for causing the microprocessor based unit to allow user access to the entertainment program signal via a display unit coupled to said microprocessor based unit; and when said at least one response is determined as not being in compliance with the pre-established compliance criteria for the prescribed medical treatment plan, providing a restrict access control signal, said restrict access control signal configured for causing the microprocessor based unit to deny user access to the entertainment program signal via the display unit.

7. The method as claimed in claim 6, further comprising retrieving the pre-established compliance criteria for the prescribed medical treatment plan for said user.

8. The method as claimed in claim 6, wherein said health-related information includes at least one of an instruction or an additional question for said user.

9. The method as claimed in claim 6, wherein said health-related information includes an educational program.

\* \* \* \* \*